(12) United States Patent
Charlton

(10) Patent No.: US 9,877,677 B2
(45) Date of Patent: Jan. 30, 2018

(54) INTEGRATED-TESTING SYSTEM

(71) Applicant: Ascensia Diabetes Care Holdings AG, Basel (CH)

(72) Inventor: Steven C. Charlton, Osceola, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 36 days.

(21) Appl. No.: 14/596,390

(22) Filed: Jan. 14, 2015

(65) Prior Publication Data

US 2015/0126838 A1 May 7, 2015

Related U.S. Application Data

(63) Continuation of application No. 12/564,513, filed on Sep. 22, 2009, now Pat. No. 8,956,308.
(Continued)

(51) Int. Cl.
| | |
|---|---|
| *A61B 5/00* | (2006.01) |
| *A61B 5/157* | (2006.01) |
| *A61B 5/15* | (2006.01) |
| *A61B 5/151* | (2006.01) |
| *A61B 5/145* | (2006.01) |

(52) U.S. Cl.
CPC ............ *A61B 5/157* (2013.01); *A61B 5/1411* (2013.01); *A61B 5/1519* (2013.01); *A61B 5/150022* (2013.01); *A61B 5/15029* (2013.01); *A61B 5/15113* (2013.01); *A61B 5/15117* (2013.01); *A61B 5/15128* (2013.01); *A61B 5/15194* (2013.01); *A61B 5/150305* (2013.01); *A61B 5/150412* (2013.01); *A61B 5/150503* (2013.01); *A61B 5/14532* (2013.01); *A61B 5/1513* (2013.01); *A61B 5/15126* (2013.01); *A61B 5/15192* (2013.01); *Y10T 29/49002* (2015.01)

(58) Field of Classification Search
CPC ............ A61B 5/15029; A61B 5/15113; A61B 5/15117; A61B 5/15126; A61B 5/15128; A61B 5/1513; A61B 5/15192; A61B 5/15194; A61B 5/157

See application file for complete search history.

(56) References Cited

U.S. PATENT DOCUMENTS 5,035,704 A * 7/1991 Lambert ............... A61B 5/1411
 600/584
5,871,494 A 2/1999 Simons
(Continued)

FOREIGN PATENT DOCUMENTS

| EP | 1 112 717 A1 | 7/2001 |
|---|---|---|
| EP | 1 120 085 A1 | 8/2001 |

(Continued)

Primary Examiner — Devin Henson
(74) Attorney, Agent, or Firm — Nixon Peabody LLP

(57) ABSTRACT

An integrated-testing system includes a meter, a lancing device and a storage case. The meter includes a housing, a display and a processor. The storage case holds the meter and the lancing device in a relatively fixed position to each other. The meter and the lancing device are maintained in the storage case in the relatively fixed position until a fluid sample is desired, at which time a first portion of the lancing device is advanced to a position external to the storage case to obtain the fluid sample and a second portion of the lancing device remains relatively fixed in the storage case while the fluid sample is obtained.

22 Claims, 13 Drawing Sheets

Related U.S. Application Data

(60) Provisional application No. 61/194,574, filed on Sep. 29, 2008.

(56) References Cited

U.S. PATENT DOCUMENTS

| | | | |
|---|---|---|---|
| 6,071,251 | A | 6/2000 | Cunningham |
| 6,206,841 | B1 | 3/2001 | Cunningham |
| 6,283,982 | B1 * | 9/2001 | Levaughn ............ A61B 5/1411 |
| | | | 606/172 |
| 6,561,989 | B2 | 5/2003 | Whitson |
| 6,603,987 | B2 | 8/2003 | Whitson |
| 6,706,159 | B2 | 3/2004 | Moerman |
| 6,781,522 | B2 | 8/2004 | Steva |
| 7,374,949 | B2 | 5/2008 | Kuriger |
| 7,378,007 | B2 | 5/2008 | Moerman |
| 7,887,682 | B2 | 2/2011 | Wang |
| 9,351,680 | B2 * | 5/2016 | Boecker ............... A61B 5/1411 |
| 2003/0211619 | A1 | 11/2003 | Olson |
| 2004/0210247 | A1 | 10/2004 | Sonoda |
| 2005/0011759 | A1 | 1/2005 | Moerman |
| 2005/0245844 | A1 | 11/2005 | Mace |
| 2006/0000549 | A1 | 1/2006 | Lang |
| 2006/0173380 | A1 | 8/2006 | Hoenes |
| 2007/0004989 | A1 | 1/2007 | Dhillon |
| 2007/0016104 | A1 | 1/2007 | Jansen |
| 2007/0213636 | A1 | 9/2007 | Kuriger |
| 2007/0233013 | A1 | 10/2007 | Schoenberg |
| 2009/0093831 | A1 | 4/2009 | Zhong |
| 2009/0099437 | A1 | 4/2009 | Yuzhakov |
| 2009/0156964 | A1 | 6/2009 | Craven |
| 2009/0326355 | A1 * | 12/2009 | Brenneman .......... A61B 5/1411 |
| | | | 600/347 |
| 2010/0021947 | A1 | 1/2010 | Emery |
| 2011/0184448 | A1 | 7/2011 | Brown |

FOREIGN PATENT DOCUMENTS

| | | |
|---|---|---|
| EP | 0 946 122 B1 | 6/2005 |
| EP | 1 611 842 A1 | 1/2006 |
| EP | 1 611 849 A1 | 1/2006 |
| WO | WO 2003/017860 A1 | 3/2003 |
| WO | WO 2004/034024 A2 | 4/2004 |
| WO | WO 2005/017800 A2 | 2/2005 |
| WO | WO 2005/045416 A1 | 5/2005 |
| WO | WO 2005/045417 A1 | 5/2005 |
| WO | WO 2005/102154 A2 | 11/2005 |
| WO | WO 2007/119900 A1 | 10/2007 |

* cited by examiner

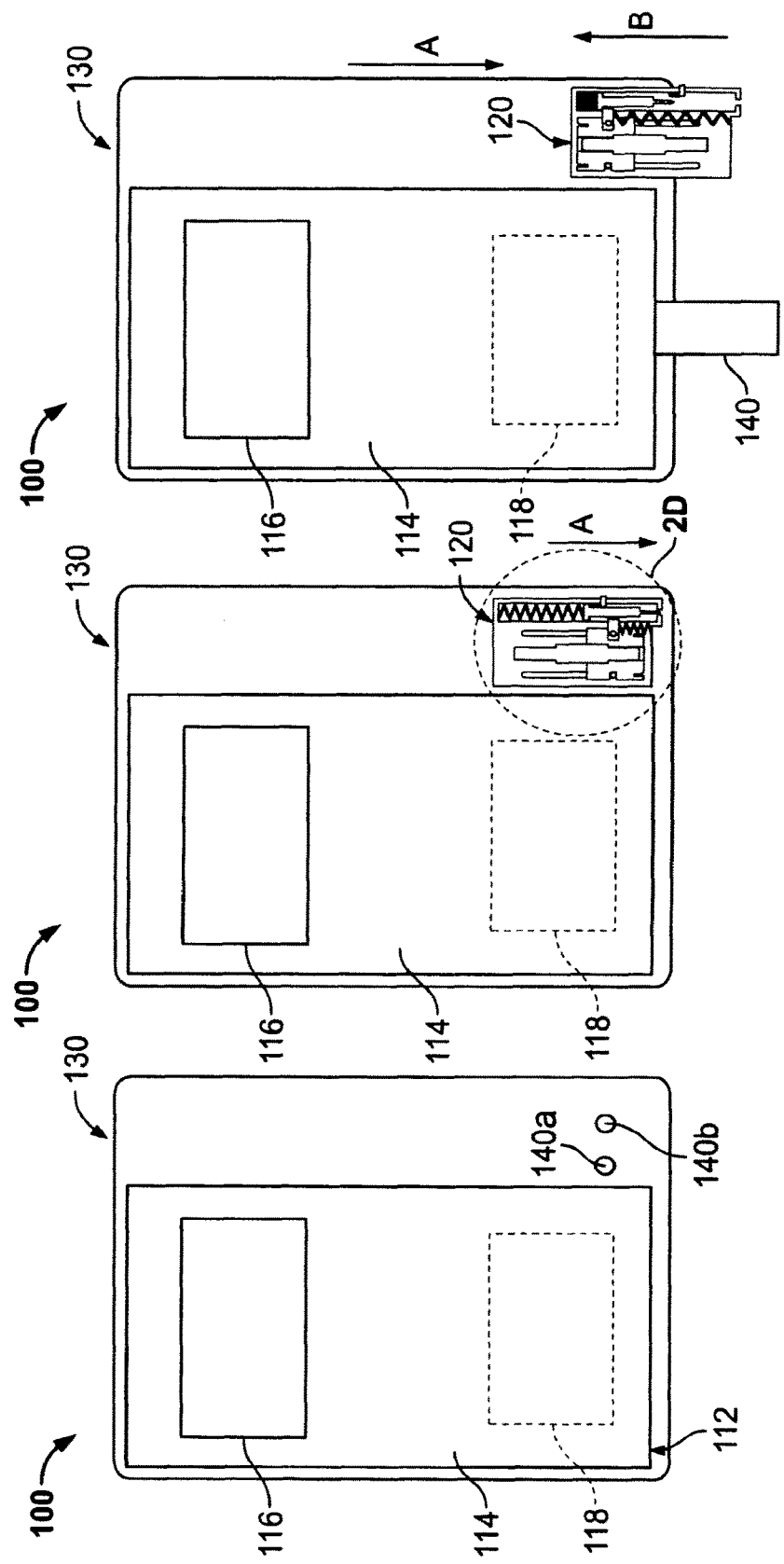

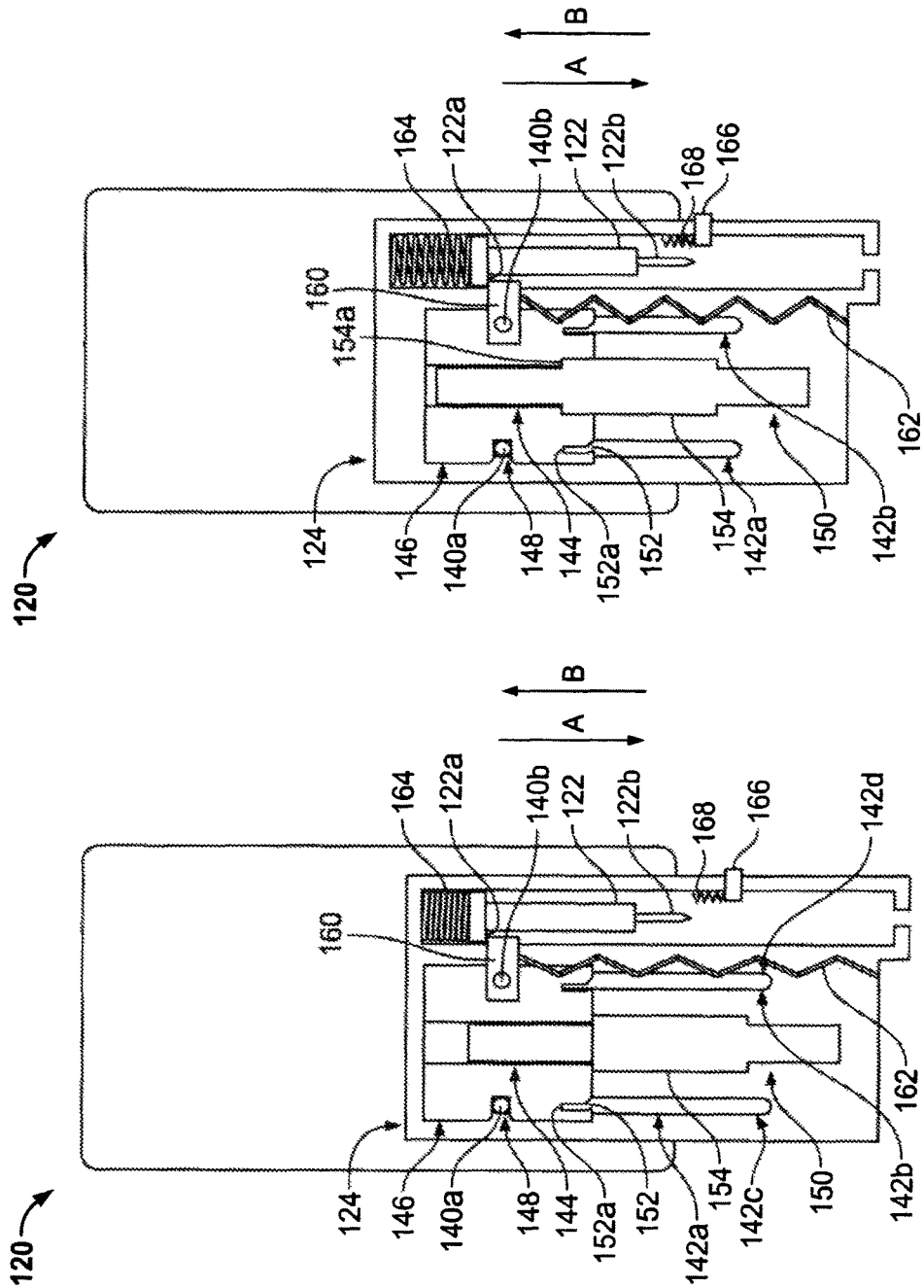

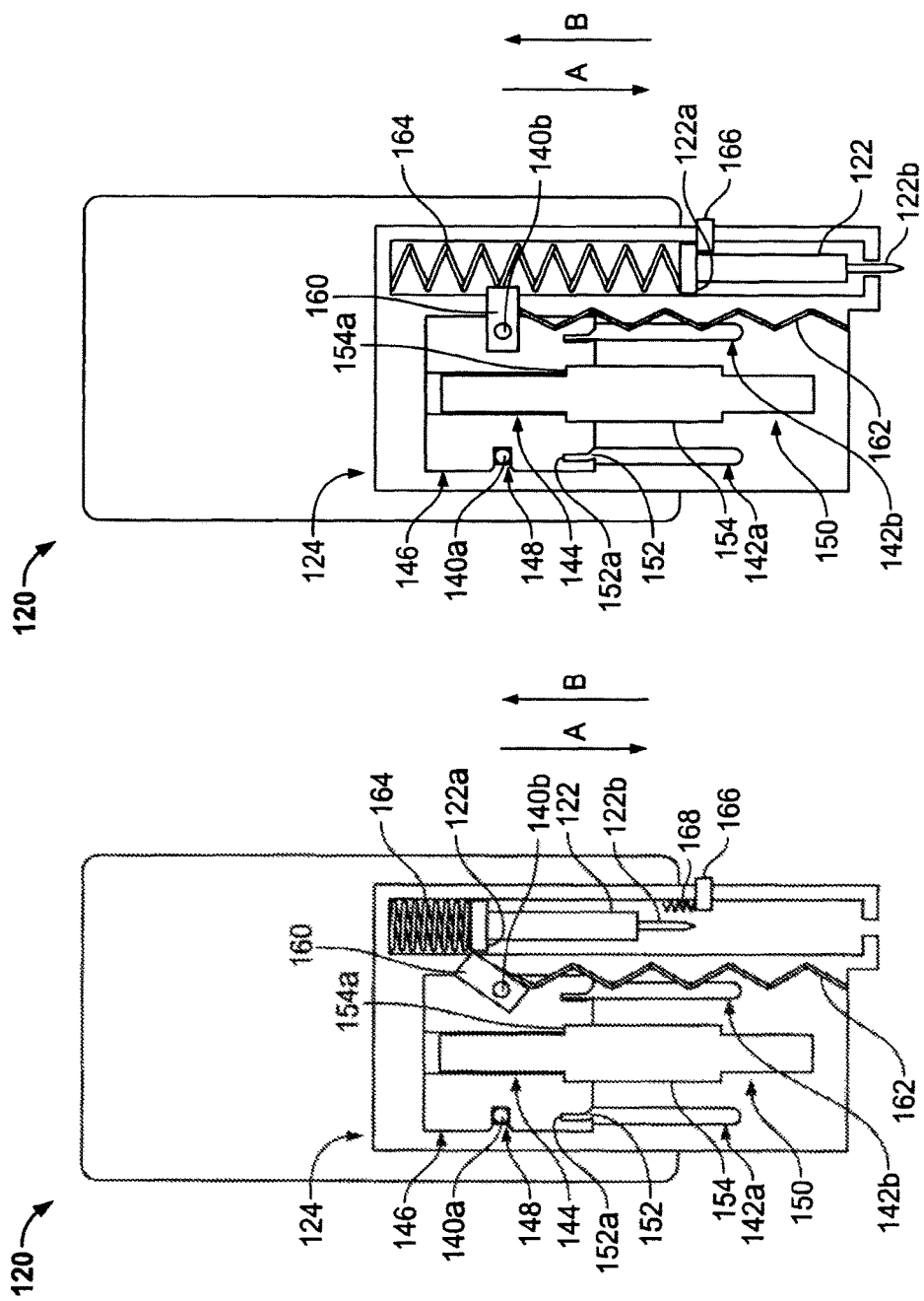

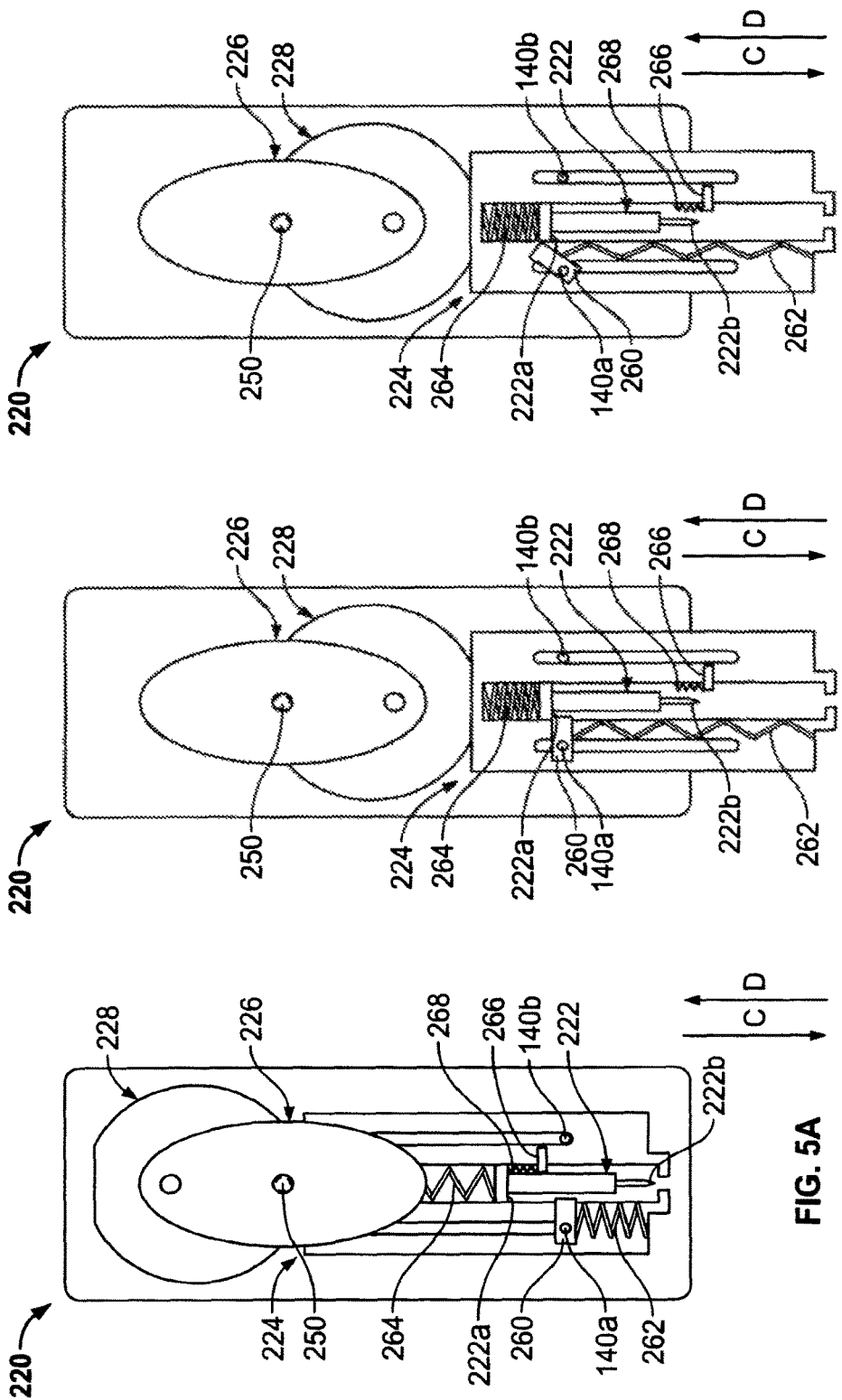

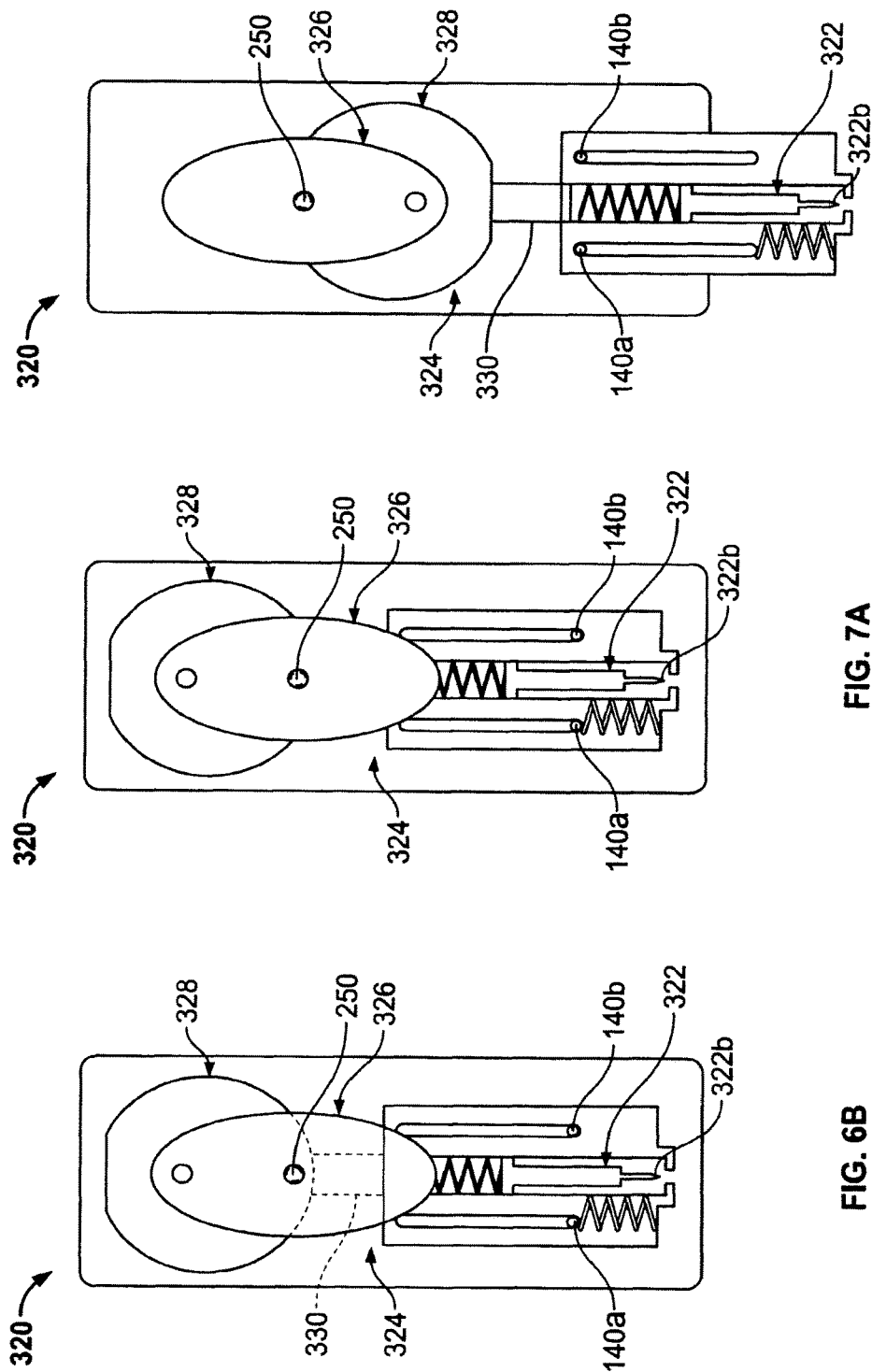

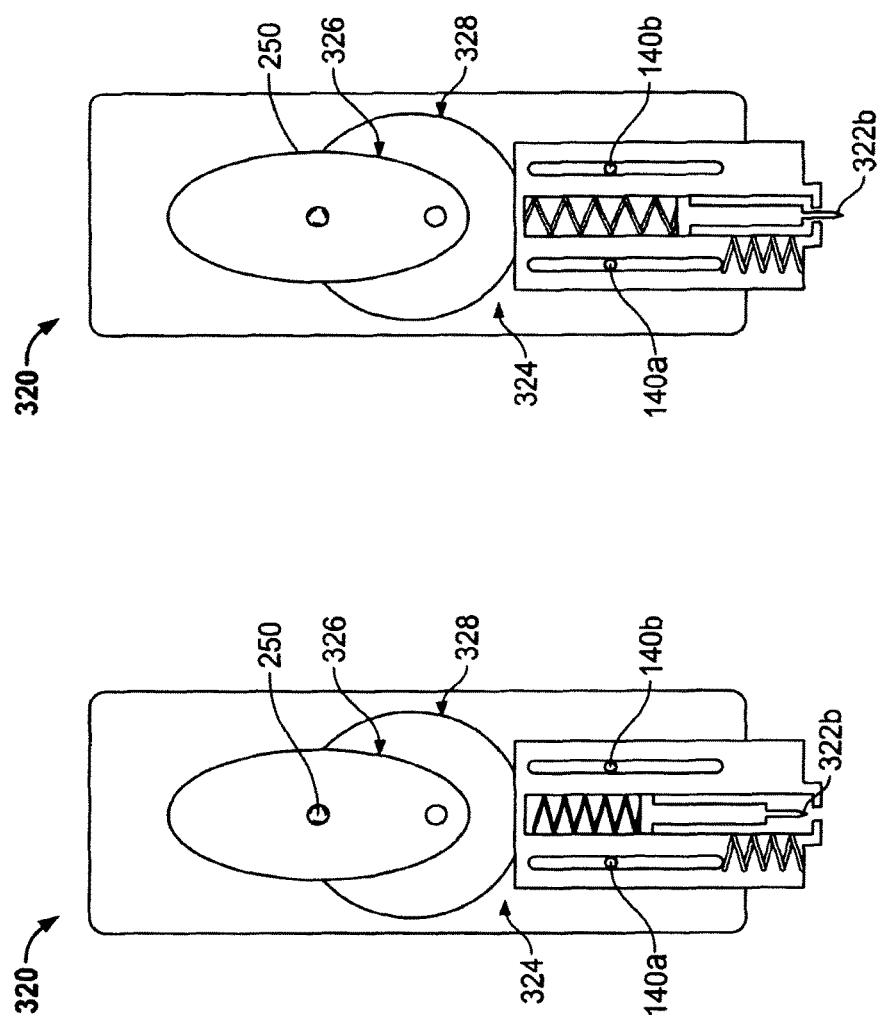

INTEGRATED-TESTING SYSTEM

CLAIM OF PRIORITY AND CROSS-REFERENCE TO RELATED APPLICATIONS

This application is a Continuation of U.S. patent application Ser. No. 12/564,513, which was filed on Sep. 22, 2009, now allowed, and claims the benefit of U.S. Provisional Patent Application No. 61/194,574, which was filed on Sep. 29, 2008, and is entitled "Integrated-Testing System", each of which is hereby incorporated by reference in its respective entirety.

FIELD OF THE INVENTION

The present invention relates generally to a testing system for determining information relating to an analyte in a fluid sample. More particularly, the present invention relates to an integrated-testing system including a meter, a lancing device and a storage case that allows a user to use the meter and lancing device while positioned in the storage case.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. Existing lancing devices use a lancet to pierce the tissue of the skin, allowing a blood sample to form on the skin's surface. The whole blood sample may then be used to determine the glucose concentration of an individual via a testing meter. In some current testing devices, the meter and the lancing device may be integrated into a single testing device. This has the advantages of having fewer items to handle during the testing. However, having the meter and lancing device within a single testing device provides for a bulkier testing device. Bulkier devices are more difficult for elderly persons, vision-impaired or less-experienced users to operate. Additionally, the testing device may be less reliable because of the added complexity involved in integration and because if either piece fails, both must be replaced.

Therefore, there exists a need for an integrated-testing system that overcomes these disadvantages.

SUMMARY OF THE INVENTION

In one embodiment, an integrated-testing system for determining information related to an analyte in a fluid sample is disclosed. The integrated-testing system includes a meter, a lancing device and a storage case. The meter includes a housing, a display and a processor. The lancing device is adapted to obtain the fluid sample. The storage case holds the meter and the lancing device in a relatively fixed position to each other. The meter and the lancing device are maintained in the storage case in the relatively fixed position until a fluid sample is desired, at which time a first portion of the lancing device is advanced to a position external to the storage case to obtain the fluid sample and a second portion of the lancing device remains relatively fixed in the storage case while the fluid sample is obtained.

In one method, information relating to an analyte in a fluid sample is determined. A storage case is provided and includes a meter and a lancing device. The storage case holds the meter and the lancing device in a relatively fixed position to each other. A first portion of the lancing device is moved to a position external to the storage case while maintaining a second portion of the lancing device in the storage case. A fluid sample is obtained by lancing in which the first portion of the lancing device remains external to the storage case and the second portion of the lancing device remains within an interior of the storage case. A fluid sample is applied to the test sensor. Information relating to the analyte in the fluid sample is determined when the meter is located in the storage case and the test sensor is located in the test-sensor opening.

BRIEF DESCRIPTION OF THE DRAWINGS

The foregoing and other advantages of the invention will become apparent upon reading the following detailed description and upon reference to the drawings.

FIG. 2a is a front plan view of a meter, storage case and lancing device-attachment feature according to one embodiment of the present invention.

FIG. 2b is a front plan view of the meter and storage case of FIG. 2a with the addition of a lancing device being a retracted position.

FIG. 2c is a front plan view of the meter and storage case of FIG. 2a with the lancing device of FIG. 2b extended and cocked ready for use.

FIGS. 3a-3f are front plan views of the lancing device of FIG. 2d in a sequence of operational positions according to one method.

FIGS. 5a-5d are front plan views of the lancing device of FIG. 4d in a sequence of operational positions according to one method.

FIG. 6b is an enlarged view of the lancing device to be used with the meter and storage case of FIG. 6a.

FIGS. 7a-7d are front plan views of the lancing device of FIG. 6b in a sequence of operational positions according to one method.

Figure 1A:
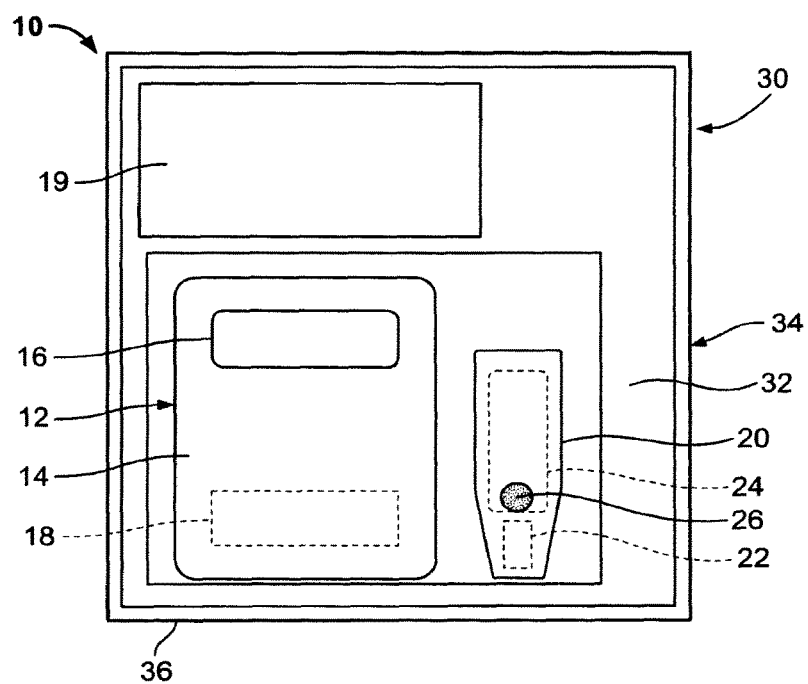
FIG. 1a is a front plan view of an integrated-testing system including a storage case, a meter and a lancing device according to one embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Figure 1B:
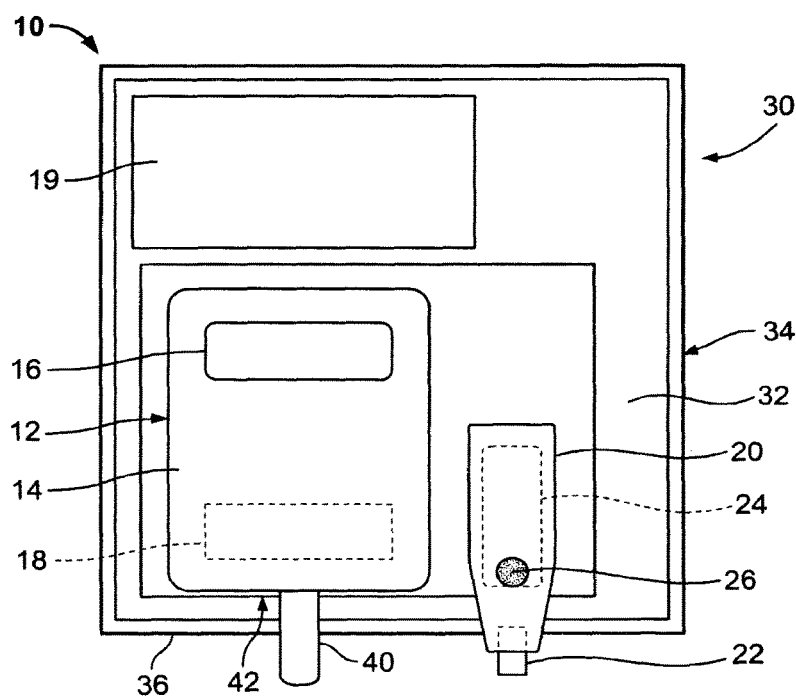
FIG. 1b is a front plan view of the integrated-testing system of FIG. 1a showing the lancing device in a lancing position.
Figure 1C:
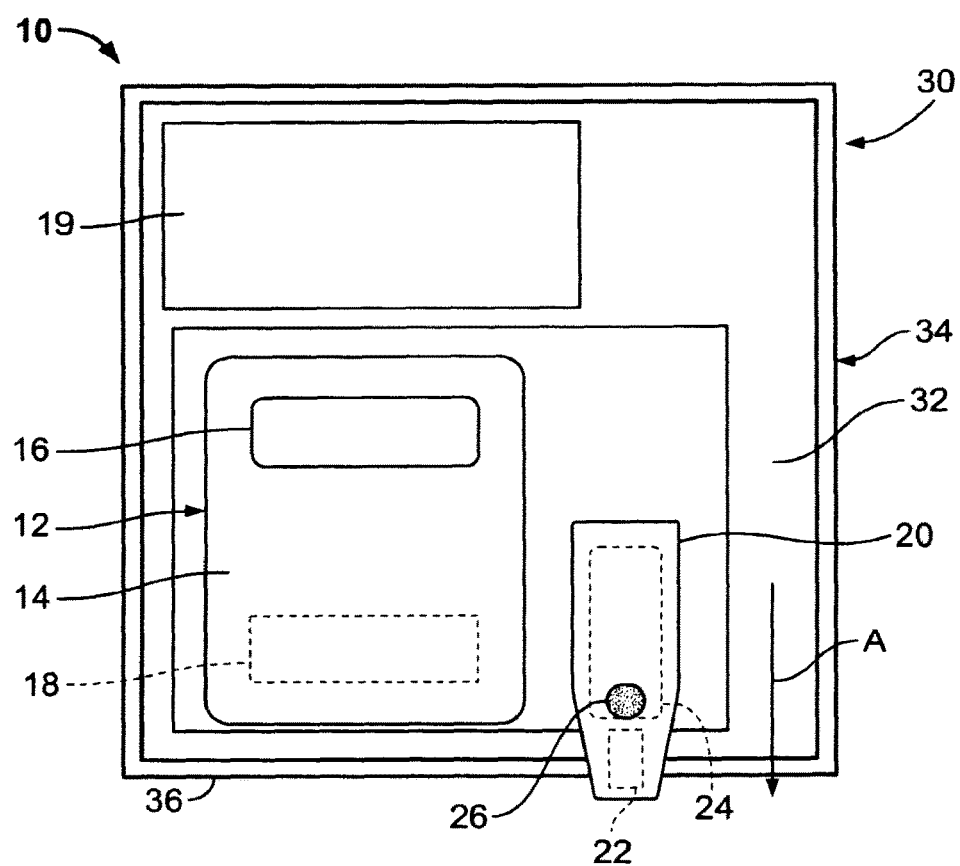
FIG. 1c is a front plan view of the integrated-testing system of FIG. 1a showing the lancing device in a post-lancing position before being retracted within the storage case.

FIGS. 1a-1c illustrate an embodiment of the integrated-testing system 10 for determining information (i.e., a concentration) relating to an analyte in a fluid sample. The integrated-testing system 10 comprises a meter 12 including a housing 14, a display 16 and a processor 18. The integrated-testing system 10 may further include a storage area 19. As shown in FIG. 1b, the fluid sample may be applied to a test strip 40 through a test-sensor opening 42 in the meter. The fluid sample is analyzed with the meter 12 to determine the concentration of the analyte to be examined. Such results may be shown on the display 16, which is typically an LCD display, but may be another type of display. The test sensors may be stored in the storage area 19. Examples of the types of analytes that may be collected include glucose, lipid profiles (e.g., cholesterol, triglycerides, LDL and HDL), microalbumin, hemoglobin $A1_c$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

The integrated-testing system 10 further includes a lancing device 20 for obtaining the fluid sample. The lancing device 20 includes a lancet 22 for piercing the skin of a user to obtain a fluid sample. The lancet 22 is held within the lancing device 20 when the lancet 22 is not in use, so as to shield the user from injury as well as to assist in preventing or inhibiting contamination. The lancing device 20 typically includes a lancing mechanism 24 for positioning the lancet 22 to take a fluid sample. The lancing mechanism 24 may include a button 26 to momentarily extend the lancet 22 from the lancing device 20 and lance the skin of the user. In another aspect, the lancing may be momentarily extended from the lancet 22 by providing pressure against a surface (e.g., a finger).

The meter 12 and the lancing device 20 of FIGS. 1a-1c are housed in a storage case 30. The storage case 30 may include a relatively rigid base portion 32 and a relatively flexible portion 34. The relatively rigid base portion 32 may be made of a polymeric material such as molded-polymeric material. Polymeric materials that may be used in forming the storage case include polycarbonate, ABS, polyethylene terephthalate (PET), polyvinyl chloride (PVC), thin metals or combinations thereof. The relatively rigid base portion may include pins, guides, clips or other components that connect with the lancing device to control movement and operation of the lancing device. Additionally, the relatively rigid base portion may further include, for example, clips, guides, elastomeric attachments or other attachments for holding the meter into a specific location of the storage case.

The relatively flexible portion 34 of the storage case 30 that is adapted to be manipulated to allow a user to access a front portion 36 of the meter 12 and the lancing device 20. The relatively flexible portion 34 may comprise an artificial fiber fabric (e.g., a nylon, a polyester, a vinyl or an acrylate) or a natural fabric material (e.g., canvas, cotton or rayon). The relatively flexible portion 34 is adapted to be folded, twisted, bent, pushed or otherwise maneuvered to enable the user to obtain a fluid sample via the lancing device 20. Furthermore, the flexible nature of the relatively flexible portion 34 of the storage case 30 allows the meter 12 to remain in the storage case 30 while the user inserts a test sensor 40 into the meter 12. The test sensor 40, once inserted into the meter 12, extends sufficiently from the meter 12 to receive a fluid sample for testing, as shown in FIG. 1b, and is available for receiving a fluid sample that has been obtained via the lancing device 20.

In another aspect, the storage case may omit a relatively flexible portion and instead have the storage case being made only of a relatively rigid portion. In such an aspect, the storage case includes a relatively rigid portion that is slid or hinged so as to allow the storage case to be moved in a direction to expose the meter for inserting a test sensor and exposing the lancing device to lance a user.

The integrated-testing systems of the present invention described herein are advantageous over existing systems in which the lancing device and meter are not accessible while in the storage case. In such systems, the lancing device and meter must generally be removed from the storage case before obtaining a fluid sample and placing it on the test sensor. The integrated-testing systems allow for a simpler, more convenient system for a user to access and use the meter 12 and lancing device 20 while being positioned in the storage case 30. The integrated-testing systems of the present invention further protect the meter 12 and lancing device 20 from being misplaced, broken or contaminated while being carried by a user in, for example, a purse, pocket, bag or another storage item.

The meter 12 is positioned in the storage case 30 in a relatively fixed position with respect to the lancing device 20. The meter 12 may be held and located within the storage case 30 via locating and holding features such as clips, guides, elastomeric materials or other attachment components. Similarly, the lancing device may be held and positioned in the storage case 30 via locating and holding features such as pins, guides, clips or other components.

As mentioned above, the storage case 30 holds the meter 12 and the lancing device 20 in a relatively fixed position until a fluid sample is desired. When a user desires to obtain a fluid sample, the user may advance a portion of the lancing device 20 to a position external to the storage case 30, as shown in FIG. 1b. In this position, the lancing device 20 is used to obtain a fluid sample. While the lancing device 20 is in the position shown in FIG. 1b, a user can initiate the lancing mechanism 24 by pressing the firing button 26 to eject the lancet 22 from the lancing device 20 and lance the skin of the user. Once a fluid sample is obtained, it may be applied to the test sensor 40 extending from the meter 12. FIG. 1c shows the lancet 22 after being retracted within the lancing device 20.

The lancet may be moved to a lancing position by a variety of methods. For example, the lancet may be moved by a plurality of pushing motions, rotating motions, or pulling motions.

Figure 2D:
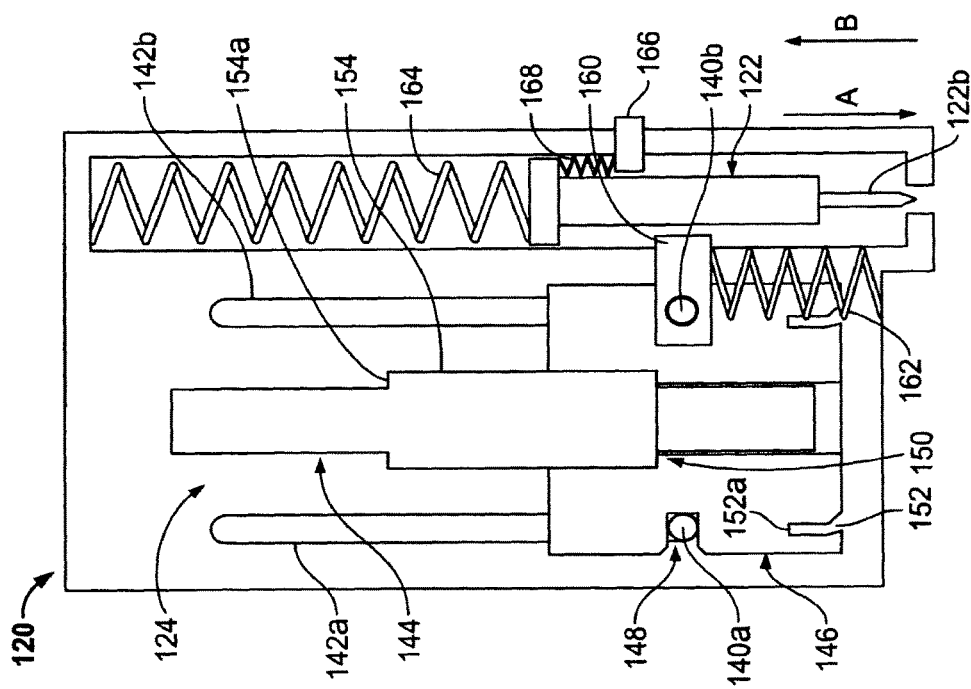
FIG. 2d is an enlarged view of the lancing device shown in FIGS. 2b, 2c.

Referring to FIGS. 2a-2d, an integrated-testing system 100 is shown according to another embodiment. The integrated-testing system 100 includes a meter 112, a lancing device 120, a storage case 130 and a plurality of pins 140a, 140b. For more clarity, the pins are enlarged in FIG. 2a as compared to FIGS. 2b, 2c. The meter 112 includes housing 114, a display 116 and a processor 118. As shown best in FIG. 2d, the lancing device 120 includes a lancet 122 and a lancet housing or body 124. The plurality of pins 140a,b is in fixed relation to the storage case 130 (FIGS. 2a-2c). The lancing device 120 is attached to the storage case 130 via the plurality of pins 140a,b as shown generally in FIGS. 2a-2c.

The lancing device 120 is moved from its position of FIG. 2b to a position in which a portion thereof is extended from the storage case 130. A non-limiting example of such a position is shown in FIG. 2c. The lancet 122 is also cocked in this position of FIG. 2c. To be moved between the positions of FIG. 2b and FIG. 2c, the lancing device 120 is moved in the direction of arrow A in FIGS. 2b and 2c. After triggering, the lancing device 120 is retracted back into the storage case. In one method, the lancing device 120 is retracted by pushing a second time in the direction of arrow A, causing the lancet body 124 to retract into the storage case 130 by moving in the direction of arrow B. Thus, in summary, a user presses down once to push out the lancet and pushed again to release and retract. It is contemplated that the lancing device may be retracted by other methods.

The lancet body 124 moves or slides with respect to the storage case 130 on the pins 140a,b, which are fixed to the storage case 130 as shown in FIGS. 2a-2c. Thus, the lancet body 124 is fixed to the storage case 130 via pins the 140a, 140b. The lancet body 124 is moved with the pins 140a,b in conjunction with the plurality of openings or slots 142a, 142b. Thus, the lancet body 124 can move the distance of the openings 142a, 142b. The cylinder 144 is fixed to the lancet body 124 so any movement of the lancet body 124 results in a corresponding movement of the cylinder 144.

A ring 146 is adapted to rotate freely around the cylinder 144. The ring 146 forms a groove 148 therearound. The groove 148 fixes the ring 146 to the pins 140a, 140b, but allows the ring 146 to rotate with respect to the cylinder 144. The ring 146 is also internally structured with a plurality of longer flutes 150 and a plurality of shorter flutes 152. The ring 146 alternates between the longer flutes 150 and the shorter flutes 152. Each of the flutes 150, 152 is adapted to mate with a fin 154 of the cylinder 144. The fin 154 is an extended width portion of the cylinder 144. Upper ends 152a of the shorter flutes 152 determine the extended position of the lancet body 124. The retracted position of the lancet body 124 may be determined either by an upper end of the longer flute 150 (if closed) or respective lower ends 142c, 142d (FIG. 3b) of the openings 142a, b. The lower ends of both the longer and shorter flutes 150, 152 are curved. As the top of the cylinder fin 154 exits a groove, this curve rotates the ring 146 to prevent or inhibit the cylinder fin 150 from re-entering the same groove but rather to enter the neighboring groove. As a result, each time the cylinder fins 154 enters the flutes of the ring 146, it alternates between a longer flute 150 and a shorter flute 152. Because the position of the ring 146 is fixed by the pins 140a, 140b the position of the lancet body 124 alternates between extended and retracted positions.

The lancing device 120 also includes a trigger 160. The trigger 160 is shown in FIG. 2d as being in a generally horizontal configuration. The trigger 160 is held in this position by a body-retraction spring 162, which also assists in retracting the lancet body 124 with respect to the storage case 130. The trigger 160 rotates upwardly (in the direction of arrow B) about one of the pins 140b to fire the lancet 122. The lancet 122 is driven by the lancet-drive spring 164 in the direction of arrow A. The travel of the lancet-drive spring 164 is limited by a stop 166. The lancet 122 is returned to its retracted position by the lancet-return spring 168.

Figure 3A:
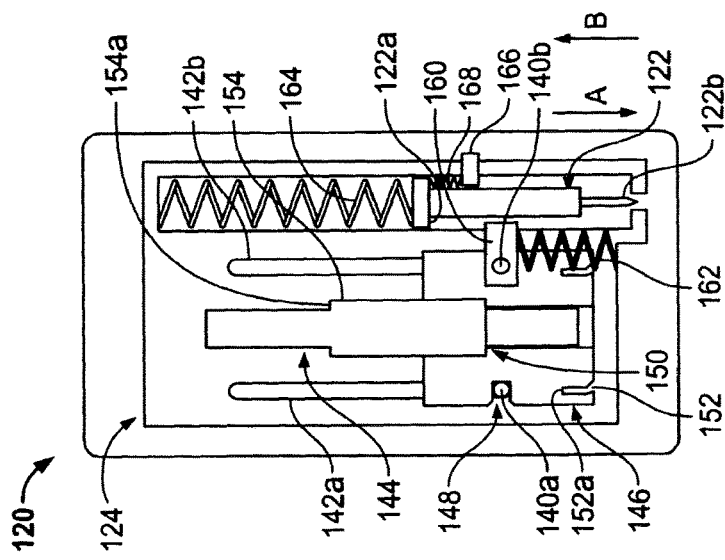

The operation sequence of the lancing device 120 according to one method is shown in FIGS. 3a-3f. FIG. 3a shows the lance body 124 in the retracted position, which is inside the storage case. Referring to FIG. 3b, the lance body 124 is moved or pushed in a generally downward direction (direction of arrow A in FIG. 3b) such that tops 154a of the cylinder fins 154 disengage from the longer flutes 150 and the ring 146 is rotated by the end curves of the longer flutes. At the same time, the trigger 160 contacts a surface 122a of the lancet 122 and pulls it back against the pressure of the lancet-drive spring 164. In FIG. 3c, the lance body 124 is released and the spring tension of the body-retraction spring 162 pulls the lance body 124 slightly back such that the cylinder fins 154 enter and stop in the short flutes 152 of the ring 146. At this point, the lancet 122 is ready for use with the lancet 122 cocked and the lancing body 124 extended out over the storage case.

Figure 3F:
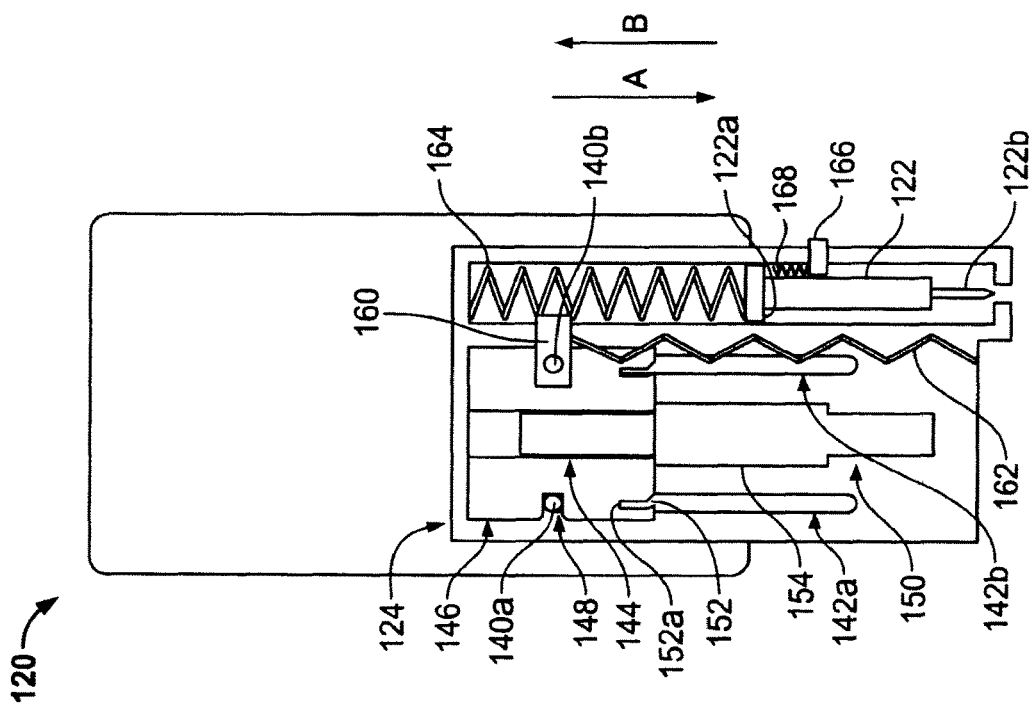

As shown in FIG. 3d, the trigger 160 is rotated and raised during firing, releasing the lancet 122, which travels rapidly downward (direction of arrow A) until being halted by the stop 166. The tip 122b of the lancet 122 momentarily extends out of the lancing body 124 (FIG. 3e) and lances the skin (e.g., a finger of a user). After the lancing, the lancing body 124 as shown in FIG. 3f is pushed forward once more so that the tops 154a of the cylinder fins 154 disengage from the shorter flutes 152 and the ring 146 is rotated by the end curves of the shorter flutes 152. Releasing the lancet body 124 allows spring tension of the body-retraction spring 162 to pull the lancing body 124 back such that the cylinder fins 154 enter and travel through the longer flutes 150 of the ring 146. During this retraction, the top of the lancet 122 rotates the trigger 160 out of the way, the lancet-return spring 168 pushes the lancet 122 off the stop 166 and the lancing device returns to the configuration of FIG. 3a.

Figure 4A:
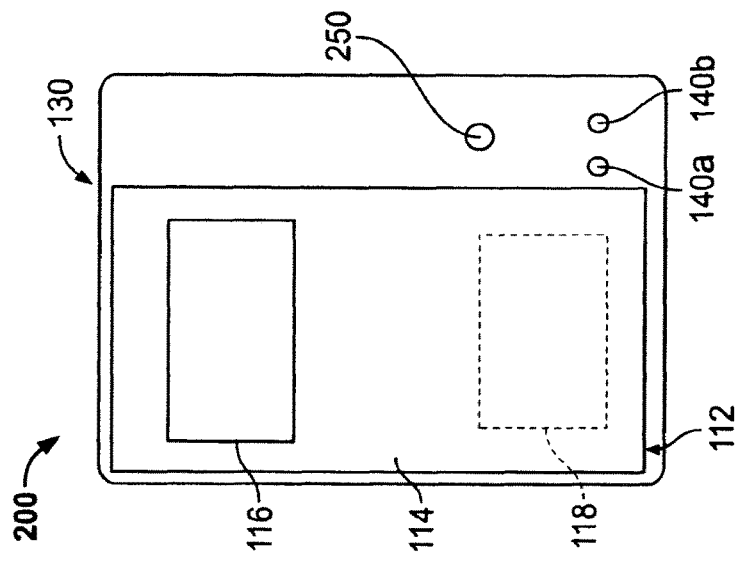
FIG. 4a is a front plan view of a meter, storage case and lancet device-attachment feature according to another embodiment of the present invention.
Figure 4C:
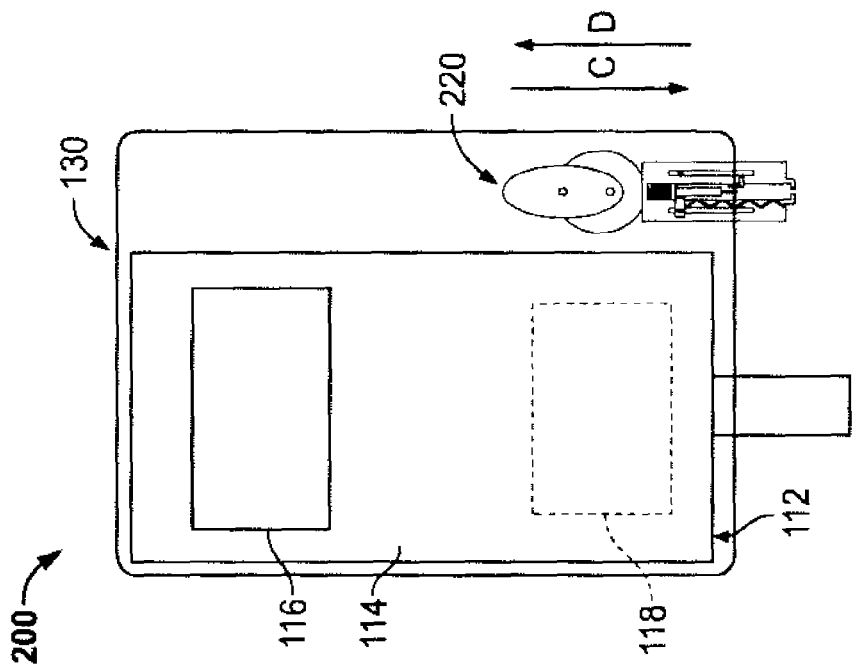
FIG. 4c is a front plan view of the meter and storage case of FIG. 4a with the lancing device of FIG. 4b extended and cocked ready for use.
Figure 4B:
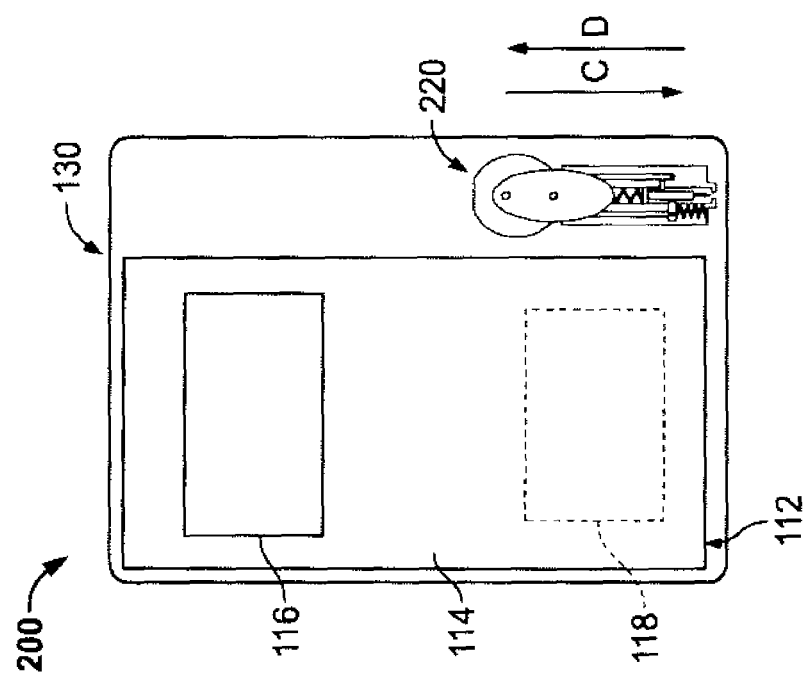
FIG. 4b is a front plan view of the meter and storage case of FIG. 4a with the addition of a lancing device being a retracted position.
Figure 4D:
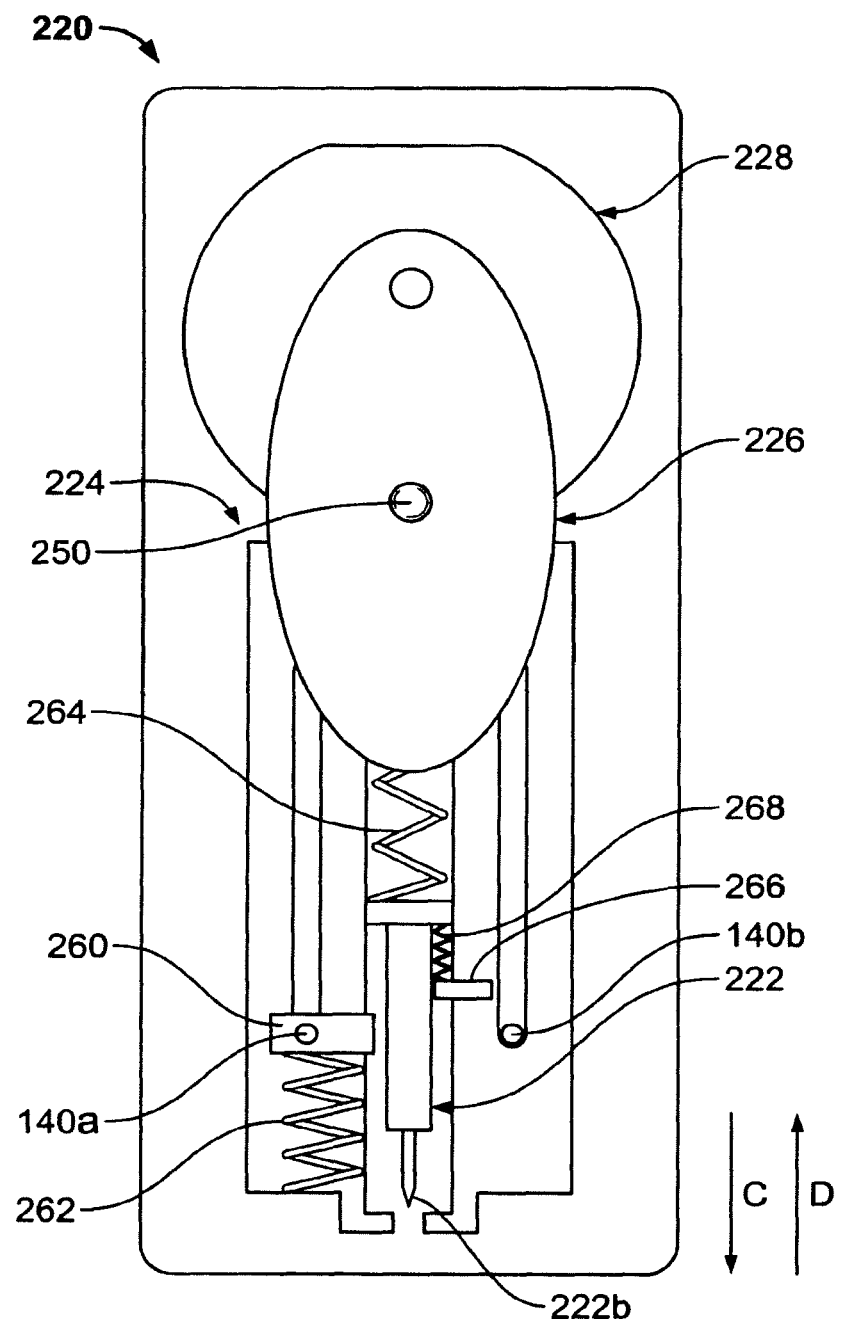
FIG. 4d is an enlarged view of the lancing device shown in FIGS. 4b, 4c.

Referring to FIGS. 4a-4d, an integrated-testing system 200 is shown according to another embodiment. The integrated-testing system 200 includes a meter 112, a lancing device 220, the storage case 130, the plurality of pins 140a,b and a pivot 250. As discussed above, the meter 112 includes the housing 114, the display 116 and the processor 118. The lancing device 220 (FIG. 4d) includes a lancet 222, a lancet housing or body 224, an operational grip 226 and a cam 228. The pins 140a,b and the pivot 250 are in fixed relation to the storage case 130. The lancing device 220 is attached to the storage case 130 via the pins 140a,b as shown in FIGS. 4a-4c. The pivot 250 assists in attaching the lancing device 220 to the storage case.

The lancing device further includes a trigger 260, a body-retraction spring 262, a lancet-drive spring 264, a stop 266 and a lancet-return spring 268. These elements function generally similar to that described above in FIG. 2d with respective elements—the trigger 160, the body-retraction spring 262, the lancet-drive spring 264, the stop 266 and the lancet-return spring 268.

In the integrated-testing system 200 of FIGS. 4a-4d, the operational grip 226 is rotated about 180° to extend the lancet body 224 from the storage case 130 and cock the lancet 222. The lancet body 224 is extended from the storage case 130 by moving or sliding in the general direction of arrow C. This is also shown by comparing the locations of the lancing device 220 in FIG. 4b and FIG. 4c. After triggering, the operating grip 226 may be further rotated by about 180° to retract the lancet body 224 back into the storage case 130. The lancet body 224 is retracted back into the storage case 130 by moving or sliding in the general direction of arrow D. The operational grip 226 of FIGS. 4b-4d attaches to the cam 228. Both the operational grip 226 and the cam 228 rotate about the pivot 250. The rotational use of the operational grip 226 is a convenient way for a user to rotate and operate the cam 228. The pivot 250 is attached to the storage case 130, resulting in rotation of the cam 228 that moves or pushes the lancet body 224 to an extended position against the tension of the body-retraction spring 262. The fixed pins 140a,b, which are attached to the storage case 130, guide the sliding motion of the lancet body 224. It is contemplated that other components may be attached to the storage case to rotate and operate the cam.

Figure 5D:
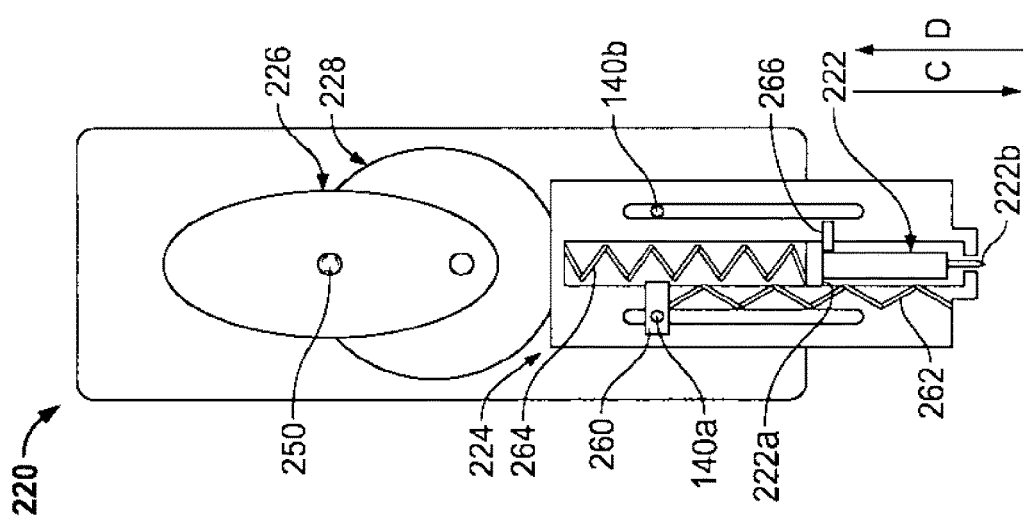

Referring to FIGS. 5a-5d, the various operational positions of the lancing device 220 of the integrated-testing system 200 are shown. Referring initially to FIG. 5a, the lancet body 224 is in the retracted position. The operational grip 226 is rotated by about 180° about the pivot 250, which also rotates the cam 228. The face of the cam 228 moves or pushes the lancet body 224 forward (in the direction of arrow C) and partially out of the storage case 130 against the tension of the body-retraction spring 262. At the same time, the trigger 260 contacts a surface 222a of the lancet 222 and moves it back against the pressure of the lance-drive spring 264. The movement of the lancet body 224 is guided by the pins 140a,b that are fixed to the storage case 130. The pin 140a is coupled with the trigger 260. At this point, as shown in FIG. 5b, the lancet 222 is ready for use. Specifically, the lancet 222 is cocked and the lancet body 224 is extended out over the storage case 130.

As shown in FIG. 5c, the trigger 260 is rotated and raised during firing, which releases the lancet 222. The lancet 222 travels rapidly in a generally downwardly fashion (in the direction of arrow C). The lancet 222 is halted by the stop 266 with the tip 222b momentarily extending out of the lancet body 224 (FIG. 5d). The tip 222b at this point can lance a portion of the skin such as, for example, a finger or an alternative-site location. The operating grip 226 is again rotated by 180°, operating the cam 228 and allowing the lancet body 224 to be retracted into the storage case 130 by tension of the body-retraction spring 262. During retraction, a top surface of the lancet 222 rotates the trigger 260 out of the way, and the lancet-return spring 268 pushes the lancet 222 off the stop 266 so as to return the lancing device 220 back to the starting configuration shown in FIG. 5a.

Figure 6A:
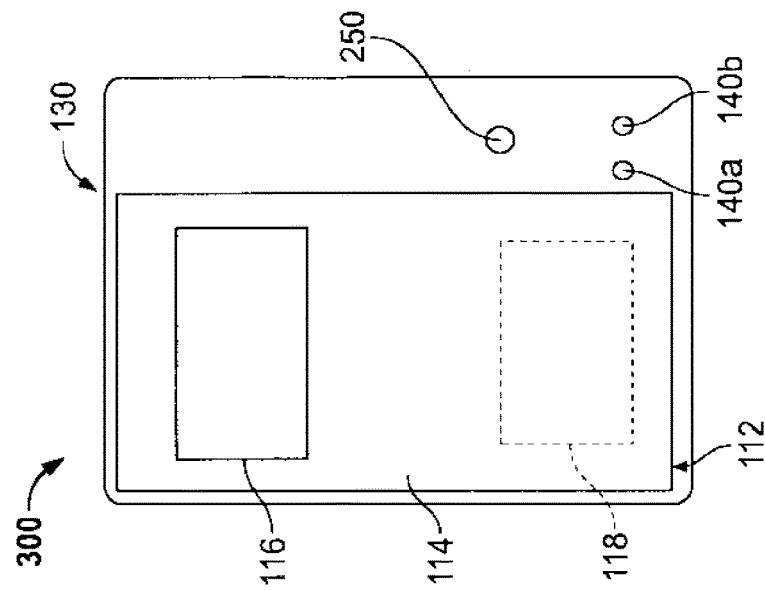
FIG. 6a is a front plan view of the meter and storage case of FIG. 4a to be used with the lancing device of FIG. 6b according to a further embodiment.

Referring to FIGS. 6a, 6b, an integrated-testing device 300 is shown according to a further embodiment. The integrated-testing system 300 includes the meter 112, a lancing device 320, the storage case 130, the pins 140a,b and the pivot 250. The lancing device 320 includes a lancet 322, a lancet housing or body 324, an operational grip 326, a cam 328 and a firing mechanism 330. The firing mechanism may be, for example, a firing button. The firing mechanism 330 of FIG. 6b is located on an opposite end to a tip 322b of the lancet 322. As discussed above, the pins 140a,b are in fixed relation to the storage case 130 and the lancet body 324 moves or slides in a similar manner as lancet body 224 discussed above. The lancing device 320 is attached to the storage case 130 via the pins 140a,b as shown in FIGS. 6a, 6b.

The integrated-testing device 300 is operated by force on the end of the lancing device 320 against the skin of a user. In the lancing device 320, the firing mechanism 330 is used to move or push the lancing device 320 against the skin of a user (e.g., a finger or alternative-site location). A user applies initial pressure resulting in the lancing device 320 being placed in a cocked position and continued pressure fires the lancet 322.

Referring to FIGS. 7a-7d, the operational sequence of the lancing device 320 to be used in an integrated-testing system is shown. Referring initially to FIG. 7a, the lancet body 324 is located in a retracted position. The operational grip 326 is rotated by about 180° via the pivot 250, which also rotates the cam 328. As shown in FIG. 7b, the face of the cam 328 moves or pushes the lancing device 320 from a storage case (e.g., storage case 130 discussed above) using the firing mechanism 330. To fire the lancing device as shown in FIGS. 7c, 7d, a user then moves or pushes the end of the lancing device against the storage case, which pushes the lancet body 324 back towards the storage case. This movement depresses the firing mechanism 330, cocking and then firing the lancet 322. The operational grip 326 is then rotated by about 180°, which moves the cam 328 and allows the lancet body 324 to be retracted into the exterior of the storage case 130.

It is contemplated that other lancing devices may be used in conjunction with the meter and the storage case in other embodiments.

As mentioned above, the embodiments described herein allow for an integrated-testing system that overcomes the disadvantages of other systems that require the removal of at least the meter, the lancing device, or both prior to obtaining a fluid sample for testing. The present embodiments provide an integrated-testing system that allows the meter and lancing device to be held in a relatively fixed position in the storage case. A flexible portion of the storage case can then be manipulated such that a user can insert a test sensor into the meter, advance the lancing device such that a portion of the lancing device is external to the storage case, obtain a fluid sample via the lancing device and apply the sample to the test sensor while the meter is held in the storage case. Furthermore, the lancing device may then be retracted within the storage case and the meter and the lancing device are maintained in the storage case until another test is desired.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. An integrated testing system for determining analyte information, the integrated testing system comprising:
    a meter including a meter housing, a display device, and a processor operable to determine information related to an analyte in a fluid sample;
    a lancing device including a lancing-device housing and a lancet, the lancet being movably mounted inside the lancing-device housing to transition between a retracted position and a lancing position, the lancet being disposed in the lancing-device housing when the lancet is in the retracted position, and the lancet protruding at least partially from the lancing-device housing when the lancet is in the lancing position;
    a storage case storing therein the meter and the lancing device, the storage case including a rigid base portion and a plurality of pins attached to the base portion, the lancing-device housing being movably mounted to the storage case via the plurality of pins, wherein the lancing device slides on the pins between an internal position, whereat the lancing-device housing is stowed inside the storage case, and an external position, whereat a first portion of the lancing-device housing protrudes from the storage case, such that a fluid sample can be lanced when the lancet is moved to the lancing position, and a second portion of the lancing-device housing remains in the storage case; and a trigger coupled to at least one of the plurality of pins, the trigger configured to engage a surface of the lancet prior to the lancet moving to the lancing position.

2. The integrated testing system of claim 1, wherein the lancing-device housing includes a plurality of slots slidably receiving therein the plurality of pins of the storage case.

3. The integrated testing system of claim 2, wherein the lancing device slides rectilinearly from the internal position to the external position.

4. The integrated testing system of claim 1, wherein the storage case further comprises a pivot rigidly attached to the base portion, and the lancing device further comprises an operational grip rotatably attached to the pivot, wherein rotating the operational grip causes the lancing device to slide on the pins between the internal and external positions.

5. The integrated testing system of claim 4, wherein the lancing device further comprises a cam rotatably attached to the lancing-device housing, and wherein the operational grip is rotatably attached to the cam.

6. The integrated testing system of claim 1, further comprising a body-retraction spring biasing the lancing device towards the internal position.

7. The integrated testing system of claim 1, wherein the storage case further includes a rigid cover portion covering at least a front of the rigid base portion to enclose the meter and the lancing device inside the storage case.

8. The integrated testing system of claim 1, wherein the storage case further includes a flexible material covering at least a front of the rigid base portion to enclose the meter and the lancing device inside the storage case.

9. The integrated testing system of claim 1, wherein the meter is rigidly mounted entirely inside the storage case.

10. The integrated testing system of claim 9, wherein the meter housing includes a test-sensor opening through which a test sensor is received, the test-sensor opening being accessible through the storage case.

11. The integrated testing system of claim 9, wherein the storage case includes one or more attaching features maintaining the meter inside the storage case, the attaching features including pins, guides, clips, or elastomeric attachments, or any combination thereof.

12. The integrated testing system of claim 1, wherein the lancing device further includes a cocking lever, the cocking lever being configured to maintain the second portion of the lancing-device housing stationary in the storage case when the first portion of the lancing-device housing protrudes from the storage case.

13. The integrated testing system of claim 1, the storage case further including a storage area configured to store a plurality of test sensors.

14. The integrated testing system of claim 1, wherein the trigger is configured to rotate about the at least one of the plurality of pins.

15. A method for assembling an integrated testing system for determining analyte information, the method comprising:

providing a meter including a meter housing, a display device attached to the meter housing, and a processor attached to the meter housing, the processor being operable to determine information related to an analyte in a fluid sample;

providing a lancing device including a lancing-device housing and a lancet, the lancet being movably mounted inside the lancing-device housing to transition between a retracted position and a lancing position, the lancet being disposed in the lancing-device housing when the lancet is in the retracted position, and the lancet protruding at least partially from the lancing-device housing when the lancet is in the lancing position; and providing a storage case including a rigid base portion and a plurality of pins rigidly attached to the base portion;

mounting the meter to the storage case;

mounting the lancing device to the storage case via the plurality of pins, wherein the lancing device is configured to slide on the pins between an internal position, whereat the lancing-device housing is stowed inside the storage case, and an external position, whereat a first portion of the lancing-device housing protrudes from the storage case, such that a fluid sample can be lanced when the lancet is moved to the lancing position, and a second portion of the lancing-device housing remains in the storage case; and coupling a trigger to at least one of the plurality of pins, the trigger configured to engage a surface of the lancet prior to the lancet moving to the lancing position.

16. The method of claim 15, wherein the lancing-device housing includes a plurality of slots slidably receiving therein the plurality of pins when the lancing device is mounted to the storage case.

17. The method of claim 15, wherein the storage case further comprises a pivot rigidly attached to the base portion, and the lancing device further comprises an operational grip, the method further comprising rotatably attaching the operational grip to the pivot such that rotating the operational grip causes the lancing device to slide on the pins between the internal and external positions.

18. The method of claim 17, wherein the lancing device further comprises a cam rotatably attached to the lancing-device housing, and wherein the operational grip is rotatably attached to the cam.

19. The method of claim 15, further comprising attaching a body-retraction spring to the storage case, the body-retraction spring biasing the lancing device towards the internal position.

20. The method of claim 15, further comprising storing a plurality of test sensors in a storage area of the storage case.

21. A glucose testing system for determining a glucose concentration in a fluid sample received by a test strip, the glucose testing system comprising:

a meter with a meter housing, an electronic display device mounted on the meter housing, a processor stowed within the meter housing, and a test sensor opening defined in the meter housing and configured to receive therethrough the test trip with the fluid sample, the processor being operable to determine information related to an analyte in a fluid sample;

a lancing device with a lancing-device housing and a lancet movably mounted inside the lancing-device housing to transition between a retracted position, whereat the lancet is disposed entirely inside the lancing-device housing, and a lancing position, whereat the lancet protrudes at least partially from the lancing-device housing, the lancing-device housing including a plurality of elongated slots;

a storage case storing therein the meter and the lancing device, the storage case including a rigid polymeric portion and a cover portion covering at least a front of the rigid polymeric portion, both the meter and the lancing device being movable within and removable from the storage case, the storage case including a plurality of pins rigidly attached to the base portion, the elongated slots of the lancing-device housing receiving therein the plurality of pins to thereby movably mount the lancing device in the storage case, wherein the lancing device slides on the pins between an internal position, whereat the lancing-device housing is stowed inside the storage case, and an external position, whereat a first portion of the lancing-device housing protrudes from the storage case, such that a fluid sample can be lanced when the lancet is moved to the lancing position, and a second portion of the lancing-device housing remains in the storage case; and a trigger coupled to at least one of the plurality of pins, the trigger configured to engage a surface of the lancet prior to the lancet moving to the lancing position.

22. The glucose testing system of claim 21, wherein the trigger is configured to rotate about the at least one of the plurality of pins and to engage the surface of the lancet when the lancing device is at an external position.

* * * * *